United States Patent [19]

Banknieder et al.

[11] Patent Number: 4,751,243

[45] Date of Patent: Jun. 14, 1988

[54] TOLRESTAT FOR WOUND HEALING

[75] Inventors: August R. Banknieder, Lawrenceville, N.J.; John F. Mullane, Westchester, N.Y.

[73] Assignee: American Home Products Corporation, New York, N.Y.

[21] Appl. No.: 860,618

[22] Filed: May 7, 1986

[51] Int. Cl.$^4$ ............................................. A61K 31/195
[52] U.S. Cl. ...................................... 514/562; 514/866
[58] Field of Search ................................ 514/562, 866

[56] References Cited

U.S. PATENT DOCUMENTS

| | | | |
|---|---|---|---|
| 4,439,617 | 3/1984 | Sestanj et al. | ........................ 560/39 |
| 4,568,693 | 2/1986 | Sestanj et al. | .................. 514/538 X |
| 4,600,717 | 7/1986 | York | ..................................... 514/278 |

OTHER PUBLICATIONS

S. Fukushi et al., "Reepithelialization of Denuded Corneas in Diabetic Rats", Exp. Eye Res. (1980) vol. 31, pp. 611–621.

M. B. Datiles et al. "Corneal Re-epithelialization in Galactosemic Rats", Inves. Ophthalmology & Visual Science, May 1983, vol. 24, pp. 564–569.

*Primary Examiner*—Leonard Schenkman
*Attorney, Agent, or Firm*—John W. Routh

[57] ABSTRACT

A method is disclosed for improving wound healing by administering an effective amount of tolrestat.

5 Claims, No Drawings

TOLRESTAT FOR WOUND HEALING

BACKGROUND OF THE INVENTION (a) Field of the Invention

This invention relates to a novel therapeutic use of N-[[5-(trifluoromethyl)-6-methoxy-1-naphthenyl]-thioxomethyl]-N-methylglycine. More specifically this invention relates to a method for improving wound healing in mammals.

(b) Prior Art

The active agent of this invention, N-[[5-(trifluoromethyl)-6-methoxy-1-naphthenyl]-thioxomethyl]-N-methylglycine or a therapeutically acceptable salt thereof, is disclosed in U.S. Pat. No. 4,568,693, issued Feb. 4, 1986. This active agent, hereinafter designated by its generic name tolrestat, previously has been reported to be useful in preventing or relieving diabetic complications such as cataracts, neuropathy, nephropathy and retinopathy (See U.S. Pat. No. 4,568,693). We have now found unexpectedly that tolrestat, either in its free acid form or in its therapeutically acceptable salt form, is useful for improving wound healing in mammals, and particularly mammals suffering from diabetes mellitus.

This finding, coupled with the fact that tolrestat is a relatively safe drug, renders the method of this invention particularly useful and advantageous.

SUMMARY OF THE INVENTION

According to this invention a method is provided for improving wound healing in a mammal in need of said treatment, which comprises administering to the mammal an affective amount of tolrestat, or a therapeutically acceptable salt thereof.

DETAILS OF THE INVENTION

According to the present method, tolrestat, either in its free acid form or in the therapeutically acceptable salt form, is employed as the active agent. Examples of suitable salt forms are described in U.S. Pat. No. 4,568,693 and include the sodium, potassium, magnesium, triethylamine and benzylamine salt forms. A preferred salt form is the sodium salt, i.e. tolrestat sodium.

While tolrestat or a therapeutically acceptable salt thereof can be administered alone, e.g. as a sole component of a filled capsule, it is preferred to formulate the compound in various dosage forms for oral or parenteral administration, e.g. tablets, or sterile solutions. Such formulations are described in U.S. Pat. No. 4,568,693, herein incorporated by reference in its entirety.

When utilizing tolrestat or one of its above-noted salts as agents for improving wound healing, the total dose of active agent can range from 0.1 to 20 mg per kilogram of body weight per day with a preferred dosage range of from 50 to 400 milligrams per day. Generally, a parenteral dose or an oral dose is administered in one to four applications per day. Such doses are considered to be an effective amount when, following their administration, an improvement in wound healing is experienced by the patient.

The effectiveness of tolrestat or its therapeutically acceptable salts as agents for improving wound healing has been demonstrated in laboratory animals.

EXAMPLE 1

The useful wound healing activities of tolrestat were demonstrated in tests utilizing research animals, as measured by the breaking strength of wounded skin. The tests determine the breaking strength of wounded skin in normal and experimentally induced diabetic rats. Male Sprague Dawley rats were used. There were twenty animals per experimental group.

DRUG PREPARATION AND ADMINISTRATION

The animals were fed regular rodent chow meal with or without tolrestat in accordance with their experimental treatment group and had access to water ad libitum.

One week prior to experimentation, food intake was monitored to determine the appropriate dietary mixture for each rat to receive 20 mg/kg/day of tolrestat in the diet.

To assure that all treated animals received tolrestat at the prescribed dosage, a new tolrestat diet was mixed every third day based upon the preceeding three days' food intake. Body weights and feed weights were recorded every three days. Therapy with tolrestat coincided with the induction of STZ diabetes. Experimental diabetes was induced by the injection of Streptozoticin (STZ) (60 mg/kg) via the tail vein in accordance with the method described by Junod, A. et al in an article entitled "Diabetogenic Action of Streptozoticin; Relationship of Dose to Metabolic Response" in J. of Clinical Investigation, Vol. 48, pages 2129–2139. Only rats with serum glucose levels above 300 mg/dl were included in the study.

Experimental treatment groups were as follows:
Group I—Normal Controls—regular diet
Group II—Tolrestat Controls—regular diet—tolrestat
Group III—STZ—Diabetic Controls—regular diet
Group IV—STZ—Diabetic Treated—regular diet+-tolrestat Six days after the induction of diabetes and onset of therapy, all rats were similarly wounded. Under general anesthesia, the back of the animal was clipped free of hair. The area was disinfected and a single cut incision 3 mm long was made parallel to the midline. The wound was closed with two skin sutures of Prolene. After three days, the sutures were removed.

On days 7, 14, 21 and 28 after wounding, five animals from each group were selected randomly. The rats were anesthetized and a blood sample taken for serum glucose determination.

The animals were euthanized and a square of skin 7 cm long by 7 cm wide removed from their back. The portion removed contained the wound site in the center of the square.

TENSILE STRENGTH TESTING

The skin samples were tested using an Instron Model 4201 tensile testing machine. Two samples from each animal were tested. The specimens, 3 mm wide and 7 cm long, were examined at both ends in platents with a pressure of 60 p.s.i. The specimens were pulled at a crosshead speed of 20 cm/minute.

PRESENTATION OF RESULTS

The output from the load cell in kilograms was recorded using a high speed printer. The rupture force (kg) of the wound is taken as the peak force on the load extension curve and is referred to as the tensile strength. Tensile strength is compared across treatment groups using a repeated measure design.

Results are shown in Table 1 below:

TABLE

| Mean tensile strength (Kg) of single cut skin wounds of rats | | | | |
|---|---|---|---|---|
| | DAYS AFTER WOUNDING | | | |
| | 7 | 14 | 21 | 28 |
| CONTROL | 0.48 | 1.98 | 4.47 | 8.53 |
| TOLRESTAT TREATED CONTROL | 0.57 | 1.57 | 4.18 | 9.50 |
| STREPTOZOTOCIN DIABETIC | 0.42 | 1.07 | 3.41 | 4.12 |
| TOLRESTAT TREATED STREPTOZOTICIN | 0.50 | 1.47 | 3.30 | 6.13 |

The results indicate a statistically significant difference in wound healing at 28 days between the control and tolrestat treated control groups and between the STZ diabetic and tolrestat treated STZ diabetic groups.

The method of this invention is particularly beneficial for improving wound healing in a diabetic patient suffering from diabetes mellitus.

We claim:

1. A method for improving dermal wound healing in a diabetic mammal in need of such treatment which comprises systemically administering orally or parenterally to the mammal an effective amount of tolrestat or a therapeutically acceptable salt thereof.

2. The method of claim 1 in which the effective amount of tolrestat is within the range of from 0.1 to 20 mg per kilogram of body weight.

3. The method of claim 1 in which the effective amount of tolrestat is within the range of from 50 to 400 milligrams per day.

4. The method of claim 1 in which the therapeutically acceptable salt is the sodium salt.

5. The method of claim 1 in which the mammal being treated is a human suffering from diabetes mellitus.

* * * * *